US005658919A

United States Patent [19]

Ratnaraj et al.

[11] Patent Number: 5,658,919
[45] Date of Patent: Aug. 19, 1997

[54] AQUEOUS PHARMACEUTICAL SUSPENSION AND PROCESS FOR PREPARATION THEREOF

[75] Inventors: Sheila M. Ratnaraj, North Wales; Warren L. Sunshine, Dresher, both of Pa.

[73] Assignee: McNeil-PPC, Inc., Skillman, N.J.

[21] Appl. No.: 711,140

[22] Filed: Sep. 9, 1996

Related U.S. Application Data

[63] Continuation of Ser. No. 383,542, Feb. 3, 1995, abandoned, which is a continuation of Ser. No. 48,701, Apr. 16, 1993, abandoned.

[51] Int. Cl.$^6$ .................. A61K 31/505; A61K 31/44; A61K 31/445; A61K 31/135
[52] U.S. Cl. .................. 514/269; 514/289; 514/317; 514/322; 514/357; 514/648; 514/653; 514/937
[58] Field of Search .................. 514/269, 289, 514/317, 322, 357, 648, 653, 937

[56] References Cited

U.S. PATENT DOCUMENTS

| | | | |
|---|---|---|---|
| 3,539,365 | 11/1970 | Duran et al. | 106/197 |
| 4,145,440 | 3/1979 | Fitch et al. | 514/975 |
| 4,327,076 | 4/1982 | Puglia et al. | 424/38 |
| 4,361,580 | 11/1982 | Peck et al. | 514/975 |
| 4,427,681 | 1/1984 | Munshi | 514/849 |
| 4,711,774 | 12/1987 | Denick et al. | 424/683 |
| 4,716,033 | 12/1987 | Denick | 514/770 |
| 4,717,565 | 1/1988 | Denick | 514/974 |
| 4,761,274 | 8/1988 | Denick et al. | 514/974 |
| 4,766,216 | 8/1988 | Wright | 546/7 |
| 4,772,724 | 9/1988 | Wright et al. | 548/403 |
| 4,788,220 | 11/1988 | Mody et al. | 514/557 |
| 4,822,876 | 4/1989 | Wright et al. | 514/819 |
| 4,857,324 | 8/1989 | Mir et al. | 424/690 |
| 4,882,324 | 11/1989 | Wright et al. | 514/569 |
| 4,886,669 | 12/1989 | Ventouras | 424/469 |
| 4,895,723 | 1/1990 | Amer et al. | 514/974 |
| 4,923,981 | 5/1990 | Weibel et al. | 536/56 |
| 4,975,465 | 12/1990 | Motola et al. | 514/557 |
| 4,996,222 | 2/1991 | Carlia et al. | 514/400 |
| 5,013,557 | 5/1991 | Tai | 424/493 |
| 5,024,997 | 6/1991 | Motola et al. | 514/974 |
| 5,032,393 | 7/1991 | Douglas et al. | 514/974 |
| 5,107,842 | 4/1992 | Levene et al. | 128/662.02 |
| 5,112,604 | 5/1992 | Beaurline et al. | 424/490 |
| 5,167,964 | 12/1992 | Muhammad et al. | 424/482 |
| 5,173,305 | 12/1992 | Grimberg | 424/682 |
| 5,196,436 | 3/1993 | Smith | 514/289 |
| 5,272,137 | 12/1993 | Blase | 514/54 |
| 5,281,408 | 1/1994 | Unger | 424/4 |
| 5,374,659 | 12/1994 | Gowan, Jr. | 514/557 |
| 5,409,907 | 4/1995 | Blase et al. | 514/54 |

FOREIGN PATENT DOCUMENTS

WO86/06626  11/1986  WIPO.

OTHER PUBLICATIONS

Remington's Pharmaceutical Sciences, 18th Ed., Chapter 83, Solution's, Emulsions, Suspensions and Extracts, pp. 1519–1530 (1990).

Avicel® RC/CL Microcrystalline Cellulose and Carboxymethyl Cellulose, NF, Bulletin RC–16, FMC Corp., pp. 1–8 (1986).

Chemical Abstracts, vol. 104, No. 8, Abst. II 104:52267c, pp. 79–80, Feb. 1986.

Avicel® RC–591 Microcrystalline Cellulose in Emulsions and Suspensions, FMC Corp. (1983).

DiMemo, L.M. et al., "Rheological and Colloidal Aspects of Avicel® Microcrystalline Cellulose", *Cellulose its Derivative*, Chapter 47, pp. 511–519 (1985).

The Physicians Desk Reference, 46th Ed., pp. 1156–1157 (1992).

Remington's Pharmaceutical Sciences, 16th ed., (1980) p. 1247.

Handbook of Pharmaceutical Excipients, (1986) pp. 131–133.

*Primary Examiner*—Raymond J. Henley, III
*Attorney, Agent, or Firm*—Bernard F. Plantz

[57] ABSTRACT

The present invention relates to an aqueous pharmaceutical suspension composition containing suspended acetaminophen and at least one additional pharmaceutical active, a suspension system containing xanthan gum, a mixture of microcrystalline cellulose and sodium carboxymethylcellulose and an auxiliary suspending agent selected from the group consisting of hydroxyethylcellulose and a pharmaceutically acceptable salt of carboxymethylcellulose, an effective amount of a taste-masking composition; and water, as well as a process for producing such aqueous pharmaceutical suspensions.

31 Claims, No Drawings

5,658,919

1

AQUEOUS PHARMACEUTICAL SUSPENSION AND PROCESS FOR PREPARATION THEREOF

This is a continuation of application Ser. No. 08/383,542, filed Feb. 3, 1995, now abandoned, which is a continuation application of Ser. No. 08/048,701 filed Apr. 16, 1993, now abandoned.

FIELD OF THE INVENTION

The present invention relates to aqueous pharmaceutical suspensions and, more particularly, to aqueous suspensions containing suspended acetaminophen, at least one additional pharmaceutical active, a suspending system and a taste-masking composition. This invention also relates to a process for preparing such suspensions.

BACKGROUND OF THE INVENTION

Orally administered drugs are provided to the patient in many dosage forms, including solid forms such as capsules, caplets or tablets and liquid forms such as solutions, emulsions or suspensions. Pharmaceuticals administered in solid form are usually intended to be swallowed whole. The disagreeable taste of the drug is generally not of concern when formulating swallowable dosage forms, because the pharmaceutical's taste can be easily masked with an exterior coating.

Children, older persons, and many other persons including disabled or incapacitated patients often have trouble swallowing tablets or capsules. In these situations, it is desirable to provide the drug either in a chewable solid form or a liquid form. For many patients, including pediatric and geriatric patients, a liquid oral dosage form is preferred over a chewable dosage form. A liquid dosage is especially preferred for this class of patients because of the ease with which it may be swallowed. Additionally, patients may be more inclined to comply with their medication instruction if the dosages are easier to ingest.

However, a common problem associated with liquid pharmaceutical dosage forms is the often disagreeable taste of a drug that may manifest itself when the drug is in the liquid dosage form. Sometimes, the taste of the drug in the dosage form may be overpowered by adding sweeteners or flavoring agents to the formulation. These agents mask the bitter or unpleasant taste of drugs. However, these agents are not totally effective in concealing the unpalatable taste of the pharmaceutical.

Liquid suspension dosage forms have stability problems associated with maintaining the drugs in suspension. Poorly formulated liquid pharmaceutical suspensions allow the drug to settle out as a sediment and may not properly redisperse, thereby affecting the therapeutic concentration of drug in the suspension. This may result in underdosing or overdosing of the patient, which may seriously compromise the patient's recovery.

If the liquid dosage form is a combination product containing both dissolved and suspended solid pharmaceutical actives, one active must remain suspended and the other active(s) must be uniformly distributed throughout the composition to ensure proper dosing. Additionally, the pharmaceutical suspension should be readily pourable so that the dosage is easy to administer. The requirement that a pharmaceutical suspension is readily pourable effectively places an upper limit on the viscosity of the suspension. This limitation also indirectly limits the amount of pharmaceutical actives that the suspension will suspend.

2

In view of these difficulties, it would be desirable to develop a ready-to-use pharmaceutical suspension, especially for combination products containing both dissolved and suspended solid actives, with a high degree of stability and good taste-masking characteristics. Therefore, there exists a need for a liquid dosage form that minimizes sedimentation of the suspended active ingredient, provides uniform distribution of the dissolved active ingredient and has a palatable taste.

The present invention provides a stable aqueous suspension for formulations containing suspended acetaminophen and at least one additional pharmaceutical active, which when combined with sweeteners and flavoring agents, provides a palatable liquid dosage form. This dosage form is also physicochemically stable and especially well suited for both geriatric and pediatric applications.

SUMMARY OF THE INVENTION

The present invention provides a pharmaceutical suspension containing suspended acetaminophen, at least one additional pharmaceutical active selected form the group consisting of antitussives, expectorants, antihistamines, sympathomimetics and mixtures thereof, a suspending system containing xanthan gum, a mixture of microcrystalline cellulose and sodium carboxymethylcellulose and an auxiliary suspending agent selected form the group consisting of hydroxyethylcellulose and a pharmaceutically acceptable salt of carboxymethylcellulose, and an effective amount of a taste-masking composition to provide a palatable taste to the suspension.

Another embodiment of this invention provides a process for preparing the aqueous pharmaceutical suspension. The mixture of microcrystalline cellulose and sodium carboxymethylcellulose is hydrated in an aqueous liquid to form a first liquid admixture. The xanthan gum and the auxiliary suspending agent are added to a liquid to form a second liquid admixture. The first and second liquid admixtures are combined to form the suspending system. The acetaminophen and at least one additional pharmaceutical active are added to the suspending system to form the pharmaceutical suspension.

DETAILED DESCRIPTION OF THE PREFERRED EMBODIMENTS

The present invention provides a novel suspension system particularly well suited for use in pharmaceutical suspensions. It is the applicants' discovery that a stable and pourable suspension containing acetaminophen and at least one additional pharmaceutical active can be formed by employing a suspending system of xanthan gum, a mixture of microcrystalline cellulose and sodium carboxymethylcellulose and an auxiliary suspending agent selected from the group consisting of hydroxyethylcellulose and a pharmaceutically acceptable salt of carboxymethylcellulose.

By limiting the amount of water in the suspension, the amount of acetaminophen dissolved in the suspension can be reduced. This reduction in the amount of dissolved acetaminophen reduces the need for taste-masking.

The suspending system forms a very stable and pourable suspension when it contains xanthan gum in the range of from about 0.1 to about 0.25 gram per 100 mL of suspension, a mixture of microcrystalline cellulose and sodium carboxymethylcellulose in the range of from about 0.4 to about 1.0 gram per 100 mL of suspension and a auxiliary suspending agent selected from the group consisting of about 0.01 to 0.10 gram per 100 mL of the suspension of a pharmaceutically acceptable salt of carboxymethylcellulose and about 0.1 to about 1.0 gram per 100 mL of the suspension of hydroxyethylcellulose. The weight ratio of xanthan gum to microcrystalline cellulose is preferably maintained in the range between about a 1:4 to 1:6. Preferably the suspending system contains xanthan gum in the range of from about 0.13 to about 0.15 gram per 100 mL of suspension, a mixture of microcrystalline cellulose and sodium carboxymethylcellulose in the range of from about 0.50 to about 0.75 gram per 100 mL of suspension and a auxiliary suspending agent selected from the group consisting of about 0.02 to 0.05 gram per 100 mL of the suspension of a pharmaceutically acceptable salt of carboxymethylcellulose and about 0.2 to about 0.5 gram per 100 mL of the suspension of hydroxyethylcellulose. Sodium carboxymethylcellulose is the preferred auxiliary suspending agent.

The xanthan gum suitable for use in the present invention is a high molecular weight polysaccharide produced by *Xanthomonas campestris*. Techniques and strains for producing this polysaccharide are described in U.S. Pat. Nos. 4,752,580 and 3,485,719 (the disclosures of which are hereby incorporated by reference). The xanthan gum used in the present invention should have a viscosity in a one percent salt solution of from about 1000 to about 1700 cP (mPa-sec). The one percent solution's viscosity should be measured at 25° C. with an LV model Brookfield Synchro-Lectric viscometer at 60 rpm, no. 3 spindle. Xanthan gum is available from several commercial suppliers such a R. T. Vanderbilt Company and Kelco, a division of Merck. Examples of suitable xanthan gums are Keltrol™, Keltrol™ F, Keltrol™ T, Keltrol™ TF and Keltrol™ 1000 (Keltrol is a trademark of Merck Inc.). Keltrol™, Keltrol™ TF and Keltrol™ 1000 are the xanthan gums preferred for use in pharmaceutical suspensions.

The mixture of microcrystalline cellulose and sodium carboxymethylcellulose used in the present invention is a dried coprecipitated microcrystal of cellulose and sodium carboxymethylcellulose. Sodium carbxymethylcellulose is commonly used as the coprecipitate in microcrystalline cellulose. It is preferable that sodium carboxymethylcellulose comprise in the range of from about 8 weight percent to about 19 weight percent of the total weight of the mixture. Presently preferred are microcrystalline cellulose products having in the range of from about 8 to about 14 weight percent sodium carboxymethylcellulose. These mixtures are commercially available from FMC under the trademark Avicel® CL-611, Avicel® RC-581 and Avicel® RC-591. Avicel® RC-591 is the preferred mixture of microcrystalline cellulose and sodium carboxymethylcellulose for use in the suspension. It contains about 8.3 to about 13.8 weight percent sodium carboxymethylcellulose, with the remainder being microcrystalline cellulose.

The auxiliary suspending agent used in the present invention is selected from the group consisting of hydroxyethylcellulose and a pharmaceutically acceptable salt of carboxymethylcellulose. Suitable pharmaceutically acceptable salts of carboxymethylcellulose include sodium and calcium salts of a polycarboxymethyl ether of cellulose, commercially available as sodium carboxymethylcellulose, USP and calcium carboxymethylcellulose, NF. Sodium carboxymethylcellulose, USP contains between about 6.5–7.5% by weight sodium on a dry basis and is commercially available form Aqualon Co. under the product designation Type 7HOF. The hydroxyethylcellulose is a partially substituted poly(hydroxyethyl) ether of cellulose. Hydroxyethylcellulose, NF is commercially available from Aqualon Co. under the tradename Natrosol™ 250L.

The suspending system discussed above is suitable for suspending acetaminophen powder in an aqueous solution. The particulate solids as a general guideline should have a particle diameter in the range of from about 1 micron to about 850 microns. Preferably the particle diameter will range from about 37 microns to about 420 microns (400 to 40 mesh based on U.S. standard mesh screens). However, those skilled in the art will recognize the fact that particle size of a specific particulate solid should be varied with the density of the particulate solid following the guidelines of Stokes' Law. The optimum particle size for a suspension should be determined empirically based on the end use and desired stability of the suspension.

At least one additional pharmaceutical active is included in the suspension of the present invention. This active is a pharmaceutical which may be used in combination with acetaminophen to form a cold or cough/cold formulation. Generally these actives are selected from the group consisting of antitussives, expectorants, antihistamines, sympathomimetics, and mixtures thereof.

Suitable antihistamines include chlorpheniramine maleate terfenadine, astemizole, diphenhydramine hydrochloride and mixtures thereof. Antitussives suitable for use in the present invention include dextromethorphan HBr, diphenhydramine hydrochloride and mixtures thereof. Expectorants which may be used in the invention include guaifenesin. Sympathomimetics suitable for use in this invention include pseudoephedrine hydrochloride, phenytpropanolamine and mixtures thereof. Other pharmaceutically acceptable salts of the aforementioned compounds may also be used in the present invention. Additional antitussives, expectorants, antihistamines, and sympathomimetics are described in *Remington's pharmaceutical Sciences*, Mack Publishing Co., Easton, Pa:, 18th ed., Chapters 42, 43 & 59 (1990), which is hereby incorporated by reference.

Preferably, the additional pharmaceutical actives used in combination with acetaminophen are pseudoephedrine hydrochloride, chlorpheniramine maleate, and, optionally, dextromethorphan hydrobromide. These additional pharmaceutical actives are generally in solution in the aqueous phase of the suspension.

The acetaminophen and the additional pharmaceutical active(s) are present in the suspension in therapeutic effective amounts, which are amounts that produce the desired therapeutic response upon oral administration and can be readily determined by one skilled in the art. In determining such amounts, the particular compound being administered, the bioavailability characteristics of the pharmaceutical, the dose regimen, the age and weight of the patient and other factors must be considered.

Generally the suspension may contain in total up to about 20 grams of acetaminophen and the additional pharmaceutical active per 100 mL of suspension. The amount of pharmaceutical active present in the suspension should be sufficient to provide a therapeutic amount of the active and a convenient dosage unit.

The suspension of the present invention may also include a taste-masking composition to mask the bitter taste of the actives in the composition, particularly the suspended acetaminophen. Generally the taste-masking composition contains at least one sweetening agent and at least one flavoring agent. The flavoring and coloring agents added to the mixture should be of the type and amount desired for the particular suspension to meet the preferences dictated by the intended consumer of such suspension, e.g., pediatric or adult.

Suitable sweetening agents include, but are not limited to, sugars such as monosaccharides, disaccharides and polysaccharides. Examples of suitable sugars include but are not limited to xylose, ribose, glucose, mannose, galactose, fructose, dextrose, sucrose, maltose, partially hydrolyzed starch or corn syrup solids, and sugar alcohols such as sorbitol, xylitol, mannitol, glycerin and combination thereof. Preferred as a sugar sweetener is high fructose corn syrup provided as an aqueous solution. The amount of sugar sweetener used in the suspension will vary depending on the degree of sweetening desired for the particular suspension. Generally the amount of sugar sweetener will be in the range of from 0 to about 110 grams per 100 mL of the suspension. Preferably the amount of sugar sweetener will be in the range of from about 40 grams to about 100 grams per 100 mL of suspension. Water soluble artificial sweeteners also may be employed in place of or in addition to sugar sweeteners. Examples of suitable artificial sweeteners include but are not limited to aspartame, sucralose, cyclamates, saccharin and mixtures thereof. The amount of artificial sweetener used in the suspension may vary from in the range of 0 to about 5 grams per 100 mL of suspension.

Suitable flavoring agents include natural and/or artificial flavors such as mints (i.e., peppermint, etc.,), menthol, cinnamon, vanilla, artificial vanilla, chocolate, artificial chocolate, both natural and/or artificial fruit flavors (i.e., cherry, grape, orange, strawberry, etc.,) and combinations of two or more thereof. Flavoring agents are generally provided as a minor component of the suspension in amounts effective to provide a palatable flavor to the suspension. However, flavoring agents are generally present in the suspension in amounts in the range of from 0 to about 5 grams per 100 mL of the suspension.

Optimum masking of the taste of the solid pharmaceutical active in the suspension can be achieved by limiting the amount of water in the suspension. As a minimum, the amount of water present in the suspension may be limited to that amount necessary to hydrate the mixture of microcrystalline cellulose and sodium carboxymethylcellulose. The minimum amount of water also must provide the suspension with a sufficient aqueous base to impart the desired degree of viscosity. It is preferred for taste-masking of bitter pharmaceutical(s) that the total amount of water contained in the suspension be in the range of from about 25 to about 60, preferably about 30 to about 55, grams per 100 mL of suspension.

The preferred pH of the suspension should range from about 3 to about 7. The suspension can be buffered to maintain the pH of the suspension in the desired pH range. Suitable buffers that are not chemically reactive with the other ingredients may be present in the suspension in amounts sufficient to provide the desired degree of pH buffering. Preferably the buffers will be present in the range of from 0 to 1 gram per 100 mL of the suspension.

Wetting agents also may be employed in the inventive suspension to facilitate the dispersion of hydrophobic pharmaceutical actives. The concentration of wetting agents in the suspension should be selected to achieve optimum dispersion of the pharmaceutical active within the suspension with the lowest feasible concentration of wetting agent. It should be appreciated that an excess concentration of wetting agent may cause the suspension to flocculate. Those skilled in the art are well versed in suitable empirical methods to determine the appropriate wetting agents and concentrations to achieve optimum dispersion and avoid flocculation. Suitable wetting agents are listed in the U.S. Pharmacoepia XXI.

Preservatives useful in the present invention include but are not limited to sodium benzoate, potassium sorbate, salts of edetate (also known as salts of ethylenediaminetetraacetic acid, or EDTA, such as disodium edetate) and parabens (such as methyl, ethyl, propyl and butyl p-hydroxybenzoic acids esters). The preservatives listed above are exemplary, but each preservative must be evaluated on an empirical basis, in each formulation, to assure the compatibility and efficacy of the preservative. Methods for evaluating the efficacy of preservatives in pharmaceutical formulations are known to those skilled in the art. Sodium benzoate and butylparaben are the presently preferred preservative ingredients to add to a pharmaceutical suspension containing acetaminophen although other pharmaceutically acceptable preservatives may be substituted therefor.

Preservatives are generally present in amounts of up to 1 gram per 100 mL of the suspension. Preferably the preservatives will be present in amounts in the range of from about 0.15 to about 0.5 gram per 100 mL of the suspension. For pharmaceutical suspensions containing acetaminophen it is preferred that the preservative sodium benzoate be present in the range of from about 0.1 to about 0.3 gram per 100 mL of the suspension and butylparaben be present in the range of from about 0.01 to about 0.05 gram per 100 mL of the suspension. It is most preferred that sodium benzoate be present at a concentration of 0.2 gram per 100 mL of the suspension and butylparaben be present at a concentration of 0.025 gram per 100 mL of the suspension.

Coloring agents also may be incorporated in the suspension to provide an appealing color to the suspension. The coloring agents should be selected to avoid chemical incompatibilities the other ingredients in the suspension. Suitable coloring agents for use in pharmaceutical suspensions are well known to those skilled in the art.

The suspensions also may contain one or more of the following additives defoaming agents, surfactants; electrolytes (monovalent cations are currently preferred); and sequestering agents.

As one embodiment of the present invention, hereinafter is provided a cold and a cough/cold pharmaceutical suspension containing acetaminophen. The following formulation provides a stable suspension that is pourable and has superior taste-masking characteristics:

TABLE 1

Cold and Cough/Cold Suspension[1]

| | Broad Range (g/100 mL) | Preferred Range (g/100 mL) |
|---|---|---|
| Suspending System | | |
| Xanthan Gum | 0.1–0.25 | 0.13–0.15 |
| Microcrystalline Cellulose/Sodium Carboxymethyl-Cellulose Mixture | 0.4–1 | 0.50–0.75 |
| Sodium Carboxymethylcellulose or | 0.01–0.1 | 0.02–0.05 |
| Hydroxyethylcellulose | 0.1–1.0 | 0.2–0.5 |
| Actives | | |
| Acetaminophen | 1–15 | 3.2–10 |
| Pseudoephedrine HCl | 0.1–1 | 0.3–0.94 |
| Chloropheniramine Maleate | 0.01–0.07 | 0.02–0.07 |
| Dextromethorphan HBr[2] | 0.05–0.5 | 0.1–0.32 |

TABLE 1-continued

Cold and Cough/Cold Suspension[1]

| Other Ingredients | Broad Range (g/100 mL) | Preferred Range (g/100 mL) |
|---|---|---|
| High Fructose Corn Syrup[3] | 50–90 | 60–90 |
| Sorbitol Solution[4] | 1–30 | 10–25 |
| Glycerin | 1–20 | 5–12 |
| Flavoring | 0.01–1 | 0.01–0.3 |
| Purified Water | 10–30 | 15–25 |
| Coloring | 0.001–.05 | 0.002–0.02 |
| Sodium Benzoate | 0.1–0.3 | 0.15–0.3 |
| Butylparaben | 0.01–0.05 | 0.02–0.03 |
| Citric Acid | 0.03–0.20 | 0.03–0.12 |
| Propylene Glycol | 0.1–0.5 | 0.15–0.35 |
| Malic Acid | 0.05–0.18 | 0.06–0.12 |

[1]All measurements in this table are listed in grams per 100 mL of suspension as measured at 25° C. If the volume of all the components does not equal 100 mL, the additional volume may be provided by the addition of high fructose corn syrup.
[2]The dextromethorphan HBr is omitted in the cold formulation.
[3]The solids content of high fructose corn syrup is approximately 77% by weight, of which 55% by weight is fructose.
[4]The sorbitol solution is approximately 70% by weight sorbitol.

The acetaminophen added to the suspension should be provided in a particulate form having a particle size range which permits greater than 99 percent of the particle to pass through a 40 mesh screen (U.S. standard screen). The amount of acetaminophen added to the suspension should be sufficient to provide a therapeutic amount of acetaminophen in a convenient dosage unit. The amount of acetaminophen in suspension should be in the range of from about 1 to about 15 grams per 100 mL of suspension.

The pseudoephedrine HCl, chlorpheniramine maleate and dextromethorphan HBr used in the suspension are USP grade. They are added in amounts to provide a therapeutic effect in a convenient dosage form.

The preferred sweeteners for acetaminophen suspension are high fructose corn syrup, sorbitol and glycerin. The high fructose corn syrup should be provided as an aqueous solution containing 77% by weight solids, of which 55% by weight is fructose. The amount of aqueous high fructose corn syrup percent in the acetaminophen suspension should be in the range of from about 50 to about 90 grams per 100 mL of suspension. The sorbitol also should be present as an aqueous solution containing 70% sorbitol by weight. The amount of aqueous sorbitol present in the acetaminophen suspension should be in the range of from about 1 to about 30 grams per 100 mL of the suspension.

The flavoring agent used in the acetaminophen suspension is artificial cherry or grape flavor(s). The amount of flavoring agent(s) used is an effective amount to provide a palatable flavor to the suspension. Other flavoring agents as previously described may be substituted for this flavoring agent. When artificial cherry or grape flavor(s) is used in an acetaminophen suspension it is preferred that the amount of artificial cherry or grape flavor(s) in the suspension be in the range of from about 0.01 to about 0.5 grams per 100 mL of suspension.

The purified water, USP added to the suspension should be kept at a minimum, to facilitate masking the bitter taste of acetaminophen. The suspension should contain in the range of from about 10 to 30 grams of purified water, USP per 100 mL of suspension.

The preservatives present in the acetaminophen suspension are butylparaben and sodium-benzoate. Other preservatives could also be used in the suspension. The acetaminophen suspension should contain in the range of from about 0.01 to about 0.05 gram of butylparaben per 100 mL of suspension and in the range of from about 0.1 to about 0.3 gram of sodium benzoate per 100 mL of suspension.

The coloring agent present in the acetaminophen suspension are FD&C Red #40, FD&C Blue #1 and D&C Red #33. Other coloring agents can be used in the pharmaceutical suspension.

When preparing the pharmaceutical suspensions provided herein, the mixture of microcrystalline cellulose and sodium carboxymethylcellulose, xanthan gum, and the auxiliary suspending agent are adequately dispersed and hydrated to provide the desired rheological characteristic to the suspension. Hydrating the mixture of microcrystalline cellulose and sodium carboxymethylcellulose requires high shear mixing to disperse and hydrate the particles. Examples of suitable high shear mixing devices include Scott Turbon mixers, homogenizers and colloid mills. It is preferred that the mixture of microcrystalline cellulose and sodium carboxymethyl cellulose be fully dispersed in an aqueous liquid, such as the purified water, USP or a mixture of the sorbitol solution and purified water, USP, prior it mixing with other ingredients.

The xanthan gum and the auxiliary suspending agent also should be dispersed in a liquid prior to mixing with the ingredients of the suspension, but they do not require high shear mixing. Suitable dispersing liquids include purified water, USP or one of the sweetening agents, such as glycerin.

The xanthan gum and the auxiliary suspending agent liquid admixture is generally combined with the microcrystalline cellulose and sodium carboxymethyl cellulose aqueous admixture to form the suspending system before the addition of other dry components, such as the acetaminophen, other pharmaceutical actives, buffers, preservatives or colorings. When adding pharmaceutical actives of more limited solubility, such as dextromethorphan HBr, it is useful to dissolve the active in one of the other components of the composition before it is added to the suspending system. For example, dextromethorphan HBr may be dissolved in the propylene glycol before it is added to the suspending system. If, however, the pharmaceutical active is very soluble in the water, e.g., chlorpheniramine maleate, it may be added to the composition earlier in the manufacturing process, such as after the hydration of the mixture of microcrystalline cellulose and sodium carboxymethylcellulose.

To assure even dispersion of the other ingredients the addition of the other ingredients into the suspension should be performed in a stepwise manner. The mixing should be conducted in a manner that does not entrain excess air. However if excess air is entrained in the suspension, after the suspension is brought to its final volume, it may be deaerated to remove entrained air and thereby returned to its normal density. The final volume of the suspension ingredients listed above may not provide a total volume of 100 mL. The final volume may be brought to 100 mL by the addition of water or preferably one or more liquid sugar sweeteners. For taste-masking purposes it is currently preferred to use liquid sugar sweetener such as high fructose corn syrup or sorbitol to bring the suspension to its final volume.

A more detailed example of the preferred process of the invention is provided in the following examples section.

EXAMPLES

The invention will now be illustrated by examples. The examples are not intended to be limiting of the scope of the present invention but read in conjunction with the detailed and general description above, providing further understanding of the present invention and an outline of a preferred process for preparing the compositions of the invention.

Example 1

Pediatric Cold Suspension

This example discloses a pediatric cold suspension containing acetaminophen, pseudoephedrine HCl, and chloropheniramine maleate and a process for manufacturing this suspension. The ingredients contained in the suspension are as follows:

| Ingredients | g/100 mL |
| --- | --- |
| Acetaminophen USP Powder | 3.2 |
| Pseudoephedrine HCl USP | 0.3 |
| Chlorpheniramine Maleate USP | 0.02 |
| High Fructose Corn Syrup 55 (HFCS 77% by wt.) | 73.0 |
| Purified Water USP | 20.0 |
| Sorbitol Solution USP 70% | 20.0 |
| Glycerin USP | 10.0 |
| Xanthan Gum NF (Keltrol 1000, Kelco) | 0.14 |
| Microcrystalline Cellulose/Sodium Carboxymethylcellulose Mixture NF (Avicel RC 591, FMC) | 0.56 |
| Sodium Carboxymethylcellulose NF (7H0F, Aqualon) | 0.03 |
| Butylparaben NF | 0.025 |
| Sodium Benzoate NF | 0.2 |
| Propylene Glycol USP | 0.25 |
| Malic Acid NF | 0.076 |
| Citric Acid USP (Anhydrous Powder) | 0.038 |
| Coloring | 0.002 |
| Artificial Grape Flavoring | 0.2 |

MANUFACTURING PROCESS 1. 1000 grams of the sorbitol solution and 975 grams of the purified water were poured into an appropiate size stainless steel container. 28 grams of the microcrystalline cellulose/sodium carboxymethylcellulose mixture (Avicel® RC 591) was added while mixing with a high-shear mixer for a period of 25 minutes. At the conclusion of the hydration period, 10.0 g of sodium benzoate and 1 gram of chlorpheniramine maleate were added and mixed until dissolved in the mixture.
2. The solution formed in step 1 was added to an appropriate size stainless steel container containing 3500 grams of the high fructose corn syrup and mixed with a high shear mixer.
3. 7 grams of xanthan gum, 1.5 grams of sodium carboxymethylcellulose and 500 grams of glycerin were added to an appropriate size stainless container and mixed with a high shear mixer. This mixture was then combined with the solution formed in step 2 and mixed with a high shear mixture.
4. 12.5 grams of propylene glycol and 1.25 grams of butylparaben were mixed in a glass beaker and then added to the solution formed in step 3.
5. 15 grams of pseudoephedrine HCl were added to the admixture produced in step 4 and mixed with a high shear mixer until all of the pseudoephedrine HCl was dissolved.
6. 160 grams of the acetaminophen powder was poured into the admixture produced in step 5 and mixed with the high mixer until the acetaminophen was evenly dispersed.
7. 0.1 gram of the coloring was dissolved in 25 grams of the purified water and mixed into the admixture produced in step 6. 1.9 grams of citric acid 3.8 grams of malic acid, and 10 grams of the flavoring were then added and mixed until completely dissolved in the admixture.
8. The final volume of the admixture was adjusted to the final 5 liter volume by adding high fructose corn syrup and then mixed with the high shear Scott mixer. The resulting suspension was then deaerated in an automatic vacuum deaerator.

The resulting pediatric cold suspension was physically stable (no flocculation or separation) at −20° to 40° C. freeze-thaw cycling for 10 weeks and at 40° C. for 10 weeks. This suspension had a pH of 4.15, viscosity of 3510 centiposes (Brookfield LV Viscometer, No. 31 RV spindle at 1½ RPM) and a density of 1.281 g/mL. The suspension was pourable and had a palatable taste.

Example 2

Pediatric Cough & Cold Suspension

This example discloses a pediatric cough and cold suspension containing acetaminophen, pseudoephedrine HCl, chloropheniramine maleate and dextromethorphan HBr and a process for manufacturing this suspension. The ingredients contained in the suspension are as follows:

| Ingredients | g/100 mL |
| --- | --- |
| Acetaminophen USP Powder | 3.2 |
| Pseudoephedrine HCl USP | 0.3 |
| Chlorpheniramine Maleate USP | 0.02 |
| Dextromethorphan HBr USP | 0.1 |
| High Fructose Corn Syrup 55 (HFCS 77% by wt.) | 73.0 |
| Purified Water USP | 20.0 |
| Sorbitol Solution USP 70% | 20.0 |
| Glycerin USP | 10.0 |
| Xanthan Gum NF (Keltrol 1000, Kelco) | 0.14 |
| Microcrystalline Cellulose/Sodium Carboxymethylcellulose Mixture NF (Avicel RC 591, FMC) | 0.56 |
| Sodium Carboxymethylcellulose NF (7H0F, Aqualon) | 0.03 |
| Butylparaben NF | 0.025 |
| Sodium Benzoate NF | 0.2 |
| Propylene Glycol USP | 0.25 |
| Citric Acid USP (Anhydrous Powder) | 0.075 |
| Coloring | 0.02 |
| Artificial Cherry Flavoring | 0.18 |

MANUFACTURING PROCESS

The ingredients were mixed together following the procedure set forth in Example 1. However, cherry flavor was substituted for the grape flavor used in Example 1. Additionally, dextromethorphan HBr was added to the admixture in step 4 with the butylparaben and propylene glycol, and malic acid was omitted.

The resulting pediatric cough/cold suspension was physically stable (no flocculation or separation) at −20° to 40° C. freeze-thaw cycling for 12 weeks and at 40° C. for 12 weeks. This suspension had a pH of 4.45, viscosity of 3910 centiposes (Brookfield LV Viscometer, No. 31 RV spindle at 1½ RPM) and a density of 1.277 g/mL. The suspension was pourable and had a palatable taste.

Example 3

Adult Cough & Cold Suspension

This example discloses an adult cough/cold suspension containing acetaminophen, pseudoephedrine HCl, and dextromethorphan HBr and a process for manufacturing this suspension. The ingredients contained in the suspension are as follows:

| Ingredients | g/100 mL |
| --- | --- |
| Acetaminophen USP Powder | 4.33 |
| Pseudoephedrine HCl USP | 0.40 |
| Dextromethorphan HBr USP | 0.20 |
| High Fructose Corn Syrup | 87.00 |
| (77% solids by wt. of which 55% is fructose) | |
| Purified Water USP | 20.00 |
| Sorbitol Solution USP 70% | 10.00 |
| Glycerin USP | 5.00 |
| Xanthan Gum NF (Keltrol 1000, Kelco) | 0.14 |
| Microcrystalline Cellulose/Sodium Carboxy-methylcellulose Mixture NF | 0.56 |
| (Avicel RC-591, FMC) | |
| Sodium Carboxymethylcellulose NF | 0.03 |
| (7H0F, Aqualon) | |
| Butylparaben NP | 0.025 |
| Sodium Benzoate NF | 0.20 |
| Propylene Glycol USP | 0.25 |
| Citric Acid USP (Anhydrous Powder) | 0.20 |
| Coloring | 0.006 |
| Flavoring Agents | q.s. |

MANUFACTURING PROCESS

The adult cough-cold suspension was prepared as follows:
1. Avicel RC-591 (28.0 g), sodium benzoate NF (10.0 g), and coloring agent (0.3 g) were dispersed in 950.0 g of purified water USP using a propeller mixer.
2. In a separate vessel, xanthan gum NF (7.0 g) and sodium carboxymethylcellulose type 7H0F (1.5 g) were dispersed in glycerin USP (250 g) with a propeller mixer.
3. In a third (small) vessel, butylparaben NF was dissolved in propylene glycol (12.5 g) using a magnetic stirrer. This mixture is then added to the dispersion prepared in step 2.
4. The xanthan gum dispersion (from steps 2 and 3) was then added to the Avicel RC-591 dispersion (from step 1) and subjected to high shear mixing until the gums are completely hydrated.
5. High fructose corn syrup 55% (3.5 kg) and sorbitol solution USP 70% (500 g) were added to the mixture with continued high shear mixing until uniform.
6. Acetaminophen USP powder (216.5 g), dextromethorphan HBr USP (10.0 g), and pseudoephedrine HCl USP (20.0 g) were added with continued mixing, followed by citric acid USP anhydrous (10.0 g) predissolved in 50 g of purified water USP and flavoring agents.
7. The batch was brought to final weight with additional high fructose corn syrup 55% and mixed to uniformity.

Example 4

Adult Cough & Cold Suspension

This example discloses an additional adult cough/cold suspension containing acetaminophen, pseudoephedrine HCl, and dextromethorphan HBr and a process for manufacturing this suspension. The ingredients contained in the suspension are as follows:

| Ingredients | g/100 mL |
| --- | --- |
| Acetaminophen USP Powder | 4.33 |
| Pseudoephedrine HCl USP | 0.40 |
| Dextromethorphan HBr USP | 0.20 |
| High Fructose Corn Syrup | 86.70 |
| (77% solids by wt. of which 55% is fructose) | |

-continued

| Ingredients | g/100 mL |
| --- | --- |
| Purified Water USP | 20.00 |
| Sorbitol Solution USP 70% | 10.00 |
| Glycerin USP | 5.00 |
| Xanthan Gum NF (Keltrol 1000, Kelco) | 0.14 |
| Microcrystalline Cellulose/Sodium Carboxymethylcellulose Mixture NF | 0.56 |
| (Avicel RC-591, FMC) | |
| Hydroxyethylcellulose NF | 0.30 |
| (Natrosol 250L Aqualon) | |
| Butylparaben NF | 0.025 |
| Sodium Benzoate NF | 0.20 |
| Propylene Glycol USP | 0.25 |
| Citric Acid USP (Anhydrous Powder) | 0.20 |
| Coloring | 0.006 |
| Flavoring Agents | q.s. |

MANUFACTURING PROCESS

The adult cough-cold suspension was prepared as follows:
1. Avicel RC-591 (28.0 g), sodium benzoate NF (10.0 g), and coloring agent (0.3 g) were dispersed in 950.0 g of purified water USP using a propeller mixer.
2. In a separate vessel, a dispersion xanthan gum NF (7.0 g) and hydroxyethylcellulose NF (Natrosol 250L) (15.0 g) in glycerin USP (250 g) was mixed with a propeller mixer.
3. In a third (small) vessel, butylparaben NF was dissolved in propylene glycol (12.5 g) using a magnetic stirrer. This mixture is then added to the dispersion prepared in step 2.
4. The xanthan gum dispersion (from steps 2 and 3) was then added to the Avicel RC-591 dispersion (from step 1) and subjected to high shear mixing until the gums are completely hydrated.
5. High fructose corn syrup 55% (3.5 kg) and sorbitol solution USP 70% (500 g) were added to the mixture with continued high shear mixing until uniform.
6. Acetaminophen USP powder (216.5 g), dextromethorphan HBr USP (10.0 g), and pseudoephedrine HCl USP (20.0 g) were added with continued mixing, followed by citric acid USP anhydrous (10.0 g) predissolved in 50 grams of purified water USP and suitable flavoring agents.
7. The batch was brought to final weight with additional high fructose corn syrup 55% and mixed to uniformity.

The scope of the present invention is not limited by the description, examples and suggested uses herein and modifications can be made without departing from the spirit of the invention. For example, additional medicaments may be added to the aqueous suspension to provide combination medications. Further, the pharmaceutical suspension of the invention may be utilized for non-medicament ingredients including nutrients such as vitamins and minerals.

Application of the compositions and methods of the present invention for medical and pharmaceutical uses can be accomplished by any clinical, medical and pharmaceutical methods and techniques as are presently or prospectively known to those skilled in the art. Thus, it is intended that the present invention cover the modifications and variations of the invention provided that they come within the scope of the appended claims and their equivalents.

What is claimed is:

1. A pharmaceutical suspension, comprising:
a therapeutic effective amount of suspended acetaminophen;
a therapeutic effective amount of at least one additional pharmaceutical active selected from the group consisting of antitussives, expectorants, antihistamines, sympathomimetics, and mixtures thereof;

a suspending system consisting essentially of about 0.1 to about 0.25 gram per 100 mL of the suspension of xanthan gum, about 0.4 to about 1.0 gram per 100 mL of the suspension of a mixture of microcrystalline cellulose and sodium carboxymethylcellulose, and an auxiliary suspending agent selected from the group consisting of about 0.01 to 0.10 gram per 100 mL of the suspension of a pharmaceutically acceptable salt of carboxymethylcellulose and about 0.1 to about 1.0 gram per 100 mL of the suspension of hydroxyethylcellulose;

water;

an effective amount of a taste-masking composition to provide a palatable taste to said suspension; and said suspension having a pH of about 3 to about 7.

2. The pharmaceutical suspension of claim 1 wherein the auxiliary suspending agent comprises sodium carboxymethylcellulose.

3. The pharmaceutical suspension of claim 1 wherein the at least one additional pharmaceutical active is an antihistamine selected from the group consisting of chlorpheniramine maleate, terfenadine, astemizole, diphenhydramine hydrochloride and mixtures thereof.

4. The pharmaceutical suspension of claim 1 wherein the at least one additional pharmaceutical active is an antitussive selected from the group consisting of dextromethorphan HBr, diphenhydramine hydrochloride and mixtures thereof.

5. The pharmaceutical suspension of claim 1 wherein the at least one additional pharmaceutical active is guaifenesin.

6. The pharmaceutical suspension of claim 1 wherein the at least one additional pharmaceutical active is a sympathomimetic selected from the group consisting of pseudoephedrine hydrochloride, phenylpropanolamine and mixtures thereof.

7. The pharmaceutical suspension of claim 1 wherein the at least one additional pharmaceutical active comprises pseudoephedrine hydrochloride and chlorpheniramine maleate.

8. The pharmaceutical suspension of claim 7 wherein the at least one additional pharmaceutical active further comprises dextromethorphan hydrobromide.

9. The pharmaceutical suspension of claim 1 wherein the mixture of microcrystalline cellulose and sodium carboxymethylcellulose comprises about 81 to about 91 percent of microcrystalline cellulose and about 9 to about 19 percent of sodium carboxymethyl cellulose, by weight of the total mixture.

10. The pharmaceutical suspension of claim 1 wherein the taste-masking composition comprises at least one sweetening agent and at least one flavoring agent.

11. The pharmaceutical suspension of claim 10 wherein the sweetening agent is selected from the group consisting of xylose, ribose, glucose, mannose, galactose, fructose, dextrose, sucrose, maltose, partially hydrolyzed starch solids, partially hydrolyzed corn syrup solids, sorbitol, xylitol, mannitol, glycerin, aspartame, sucralose, cyclamates, saccharin and mixtures thereof.

12. The pharmaceutical suspension of claim 1 comprising about 25 to about 60 grams per 100 mL of the suspension of water.

13. A pharmaceutical suspension, comprising:

a therapeutic effective amount of suspended acetaminophen;

a therapeutic effective amount of at least one additional pharmaceutical active selected from the group consisting of pseudoephedrine hydrochloride, chlorpheniramine maleate, dextromethorphan hydrobromide, and mixtures thereof;

a suspending system consisting essentially of about 0.1 to about 0.25 gram per 100 mL of the suspension of xanthan gum, about 0.4 to about 1 gram per 100 mL of the suspension of a mixture of microcrystalline cellulose and sodium carboxymethylcellulose, and an auxiliary suspending agent selected from the group consisting of about 0.01 to about 0.1 gram per 100 mL of the suspension of a pharmaceutically acceptable salt of carboxymethylcellulose and about 0.1 to about 1.0 gram per 100 mL of the suspension of hydroxyethylcellulose;

water;

an effective amount of a taste-masking composition comprising at least one sweetening agent and at least one flavoring agent to provide a palatable taste to said suspension; and said suspension having a pH of about 3 to about 7.

14. The pharmaceutical suspension of claim 13 wherein the auxiliary suspending agent comprises sodium carboxymethylcellulose.

15. The pharmaceutical suspension of claim 13 wherein the mixture of microcrystalline cellulose and sodium carboxymethylcellulose comprises about 81 to about 91 percent of microcrystalline cellulose and about 9 to about 19 percent of sodium carboxymethyl cellulose, by weight of the total mixture.

16. The pharmaceutical suspension of claim 13 wherein in the at least one additional pharmaceutical active comprises pseudoephedrine hydrochloride and chlorpheniramine maleate.

17. The pharmaceutical suspension of claim 16 comprising about 0.13 to about 0.15 gram per 100 mL of the suspension of xanthan gum, about 0.5 to about 0.75 gram per 100 mL of the suspension of the mixture of microcrystalline cellulose and sodium carboxymethylcellulose and about 0.02 to about 0.05 gram per 100 mL of the suspension of sodium carboxymethylcellulose.

18. The pharmaceutical suspension of claim 13 comprising about 25 to about 60 grams per 100 mL of the suspension of water.

19. A pharmaceutical suspension, comprising by gram per 100 mL of said suspension:

about 1 to about 15 acetaminophen;

a pharmaceutical active selected from the group consisting of about 0.1 to about 1 pseudoephedrine HCl, about 0.01 to about 0.07 chlorpheniramine maleate, about 0.05 to about 0.5 dextromethorphan HBr, and mixtures thereof;

about 0.1 to about 0.25 xanthan gum;

about 0.4 to about 1 of a mixture of microcrystalline cellulose and sodium carboxymethycellulose;

a suspending agent selected from the group consisting of about 0.01 to about 0.1 sodium carboxymethylcellulose and about 0.1 to about 1.0 hydroxyethylcellulose;

about 50 to about 90 high fructose corn syrup;

about 1 to about 30 sorbitol solution;

about 1 to about 20 glycerin;

about 0.01 to about 1 flavoring;

about 10 to about 30 water;

about 0.001 to about 0.05 coloring;

about 0.1 to about 0.3 sodium benzoate;

about 0.001 to about 0.05 butylparaben;

about 0.03 to about 0.20 citric acid;

about 0.1 to about 0.5 propylene glycol;

about 0.05 to about 0.18 malic acid; and said suspension having a pH of about 3 to about 7.

20. A pharmaceutical suspension, comprising:

a therapeutic effective amount of suspended acetaminophen;

a therapeutic effective amount of at least one additional pharmaceutical active selected from the group consisting of antitussives, expectorants, antihistamines, sympathomimetics, and mixtures thereof;

a suspending system consisting essentially of about 0.1 to about 0.25 gram per 100 mL of the suspension of xanthan gum, about 0.4 to about 1.0 gram per 100 mL of the suspension of a mixture of microcrystalline cellulose and sodium carboxymethylcellulose, and an auxiliary suspending agent selected from the group consisting of about 0.01 to 0.10 gram per 100 mL of the suspension of a pharmaceutically acceptable salt of carboxymethylcellulose and about 0.1 to about 1.0 gram per 100 mL of the suspension of hydroxyethylcellulose;

water; and an effective amount of a taste-masking composition to provide a palatable taste to said suspension.

21. A pharmaceutical suspension, comprising by gram per 100 mL of said suspension:

about 1 to about 15 acetaminophen;

a pharmaceutical active selected from the group consisting of about 0.1 to about 1 pseudoephedrine HCl, about 0.01 to about 0.07 chlorpheniramine maleate, about 0.05 to about 0.5 dextromethorphan HBr, and mixtures thereof;

about 0.1 to about 0.25 xanthan gum;

about 0.4 to about 1 of a mixture of microcrystalline cellulose and sodium carboxymethycellulose;

a suspending agent selected from the group consisting of about 0.01 to about 0.1 sodium carboxymethylcellulose and about 0.1 to about 1.0 hydroxyethylcellulose;

about 50 to about 90 high fructose corn syrup;

about 1 to about 30 sorbitol solution;

about 1 to about 20 glycerin;

about 0.01 to about 1 flavoring;

about 10 to about 30 water;

about 0.001 to about 0.05 coloring;

about 0.1 to about 0.3 sodium benzoate;

about 0.001 to about 0.05 butylparaben;

about 0.03 to about 0.20 citric acid;

about 0.1 to about 0.5 propylene glycol; and about 0.05 to about 0.18 malic acid.

22. A process for forming an aqueous pharmaceutical suspension comprising the steps of:

a) dispersing a mixture of microcrystalline cellulose and sodium carboxymethyl cellulose in an aqueous liquid to form a first liquid admixture;

b) dispersing xanthan gum and an auxiliary suspending agent selected from the group consisting of a pharmaceutically acceptable salt of carboxymethylcellulose and hydroxyethylcellulose in a liquid to form a second liquid admixture;

c) combining the first and second admixtures to form a suspending system consisting essentially of about 0.1 to about 0.25 gram per 100 mL of the suspension of xanthan gum, about 0.4 to about 1.0 gram per 100 mL of the suspension of a mixture of microcrystalline cellulose and sodium carboxymethylcellulose, and an auxiliary suspending agent selected from the group consisting of about 0.01 to 0.10 gram per 100 mL of the suspension of a pharmaceutically acceptable salt of carboxymethylcellulose and about 0.1 to about 1.0 gram per 100 mL of the suspension of hydroxyethylcellulose; and d) admixing said suspending system with a therapeutic effective amount of suspended acetaminophen, a therapeutic effective amount of at least one additional pharmaceutical active selected from the group consisting of antitussives, expectorants, antihistamines, sympathomimetics, and mixtures thereof and an effective amount of a taste-masking composition to provide a palatable taste to said suspension, and said suspension having a pH of about 3 to about 7.

23. The process of claim 22 wherein the auxiliary suspending agent comprises sodium carboxymethylcellulose.

24. The process of claim 22 wherein the at least one additional pharmaceutical active comprises pseudoephedrine hydrochloride and chlorpheniramine maleate.

25. The process of claim 24 wherein the at least one additional pharmaceutical active further comprises dextromethorphan hydrobromide.

26. The process of claim 22 wherein the mixture of microcrystalline cellulose and sodium carboxymethylcellulose comprises about 81 to about 91 percent of microcrystalline cellulose and about 9 to about 19 percent of sodium carboxymethyl cellulose, by weight of the total mixture.

27. The process of claim 22 wherein the taste-masking composition comprises at least one sweetening agent and at least one flavoring agent.

28. The process of claim 27 wherein the sweetening agent is selected from the group consisting of xylose, ribose, glucose, mannose, galactose, fructose, dextrose, sucrose, maltose, partially hydrolyzed starch solids, partially hydrolyzed corn syrup solids, sorbitol, xylitol, mannitol, glycerin, aspartame, sucralose, cyclamates, saccharin and mixtures thereof.

29. The process of claim 28 wherein the at least one additional pharmaceutical active further comprises dextromethorphan hydrobromide, pseudoephedrine hydrochloride and chlorpheniramine maleate, and the dextromethorphan is dissolved in glycerin before it is added to said suspending system.

30. The process of claim 22 wherein the suspension comprises about 25 to about 60 grams per 100 mL of the suspension of water.

31. A process for forming an aqueous pharmaceutical suspension comprising the steps of:

a) dispersing a mixture of microcrystalline cellulose and sodium carboxymethyl cellulose in an aqueous liquid to form a first liquid admixture;

b) dispersing xanthan gum and an auxiliary suspending agent selected from the group consisting of a pharmaceutically acceptable salt of carboxymethylcellulose and hydroxyethylcellulose in a liquid to form a second liquid admixture;

c) combining the first and second admixtures to form a suspending system consisting essentially of about 0.1 to about 0.25 gram per 100 mL of the suspension of xanthan gum, about 0.4 to about 1.0 gram per 100 mL of the suspension of a mixture of microcrystalline cellulose and sodium carboxymethylcellulose, and an auxiliary suspending agent selected from the group consisting of about 0.01 to 0.10 gram per 100 mL of the suspension of a pharmaceutically acceptable salt of carboxymethylcellulose and about 0.1 to about 1.0 gram per 100 mL of the suspension of hydroxyethylcellulose; and d) admixing said suspending system with a therapeutic effective amount of suspended acetaminophen, a therapeutic effective amount of at least one additional pharmaceutical active selected from the group consisting of antitussives, expectorants, antihistamines, sympathomimetics, and mixtures thereof and an effective amount of a taste-masking composition to provide a palatable taste to said suspension.

* * * * *